United States Patent [19]

Yang

[11] Patent Number: 4,533,636
[45] Date of Patent: Aug. 6, 1985

[54] MEDIUM FOR PLANT PROTOPLAST CULTURE

[75] Inventor: Ning-Sun Yang, Verona, Wis.

[73] Assignee: Agracetus Madison Corporation, Middleton, Wis.

[21] Appl. No.: 526,496

[22] Filed: Aug. 25, 1983

[51] Int. Cl.$^3$ .................. A01B 79/00; A01C 1/00; C12N 5/00; C12N 5/02
[52] U.S. Cl. ................... 435/240; 435/241; 435/948; 47/58
[58] Field of Search .............. 435/240, 241, 948; 47/58

[56] References Cited

FOREIGN PATENT DOCUMENTS 0905281 2/1982 U.S.S.R. ................. 435/24
8202900 9/1982 U.S.S.R. ................. 435/240

OTHER PUBLICATIONS

Kassanis et al., *Biol. Abst.*, vol. 67, (10), No. 63312, "Inhibition of Tobacco Mosaic Virus Multiplication in Tobacco Protoplasts by Rabbit Serum".

*Primary Examiner*—Thomas G. Wiseman
*Assistant Examiner*—Robin Lyn Teskin
*Attorney, Agent, or Firm*—Albert P. Halluin; Elliott Fineman; Nicholas J. Seay

[57] ABSTRACT

A culture medium and method for the isolation and culture of plant protoplasts is disclosed which includes in it a quantity of neutral mammalian blood serum. An addition of 1 to 25% serum to protoplast media results in a greater yield of viable protoplast cells, helps to protect the protoplasts in culture, and makes it possible to obtain and maintain corn protoplasts, a heretofore difficult task.

10 Claims, 1 Drawing Figure

MEDIUM FOR PLANT PROTOPLAST CULTURE

FIELD OF THE INVENTION

The present invention relates to the husbandry and maintenance of plant cell protoplasts in general, and relates, in particular, to a medium particularly adapted for the isolation, maintenance, and sustenance of plant cell protopasts in vitro and a method of using the same.

DESCRIPTION OF THE PRIOR ART

The techniques of isolating, maintaining, and culturing protoplasts of plants are becoming more widely used as a key mechanism for use in the genetic engineering of plants and for the asexual propogation of plants from protoplast cell cultures into adult normal plants. Plant cell protoplasts are viable, intact, plant cells that have been removed from their cell walls. Much effort is currently being made to develop suitable techniques for the handling and care of protoplasts through the various steps of regenerating whole plants. To begin with it is necessary to isolate viable protoplasts, i.e. by removing plant cells from the structure of the plant and by stripping from the cells their own cell walls, ideally without damaging the cytoplasmic membranes and the remainder of the cells themselves. Once isolated, the problem becomes the maintenance of active protoplasts during in vitro manipulation, especially during insertion and removal of genetic materials, if that is a part of the procedure. Once the protoplasts are obtained and manipulated or engineered as desired, the task is then to regenerate the protoplasts back into whole plant cells in culture media as a normal cell wall containing plant cells, and later as plant callus cultures and plant cell aggregates, in an attempt to start the process of reproducing whole intact and structurally normal plants.

Most of the current procedures used for the maintenance of protoplasts have been found deficient in one or more regards. In particular, no method or product has yet been developed which is reliably usable for the isolation and maintenance of protoplast cells in most cereal plants of wide economic interest such as corn and wheat. The principal difficulty in the formulation of such methods and media is the lack of knowledge about the character of any constituents or reagents which will protect plant protoplasts in general from lysis under various in vitro conditions. Typically in attempted in vitro maintenance and regeneration of plants from plant protoplast cultures, most if not all of the protoplast cells are lysed inadvertently at one or more steps during the procedure of their isolation, maintenance or handling. Even when a protoplast culture can be maintained so that some yield of protoplast cells can be achieved, the yield of viable protoplast cells is often very low. Therefore it is necessary to develop additional methods and media which are suitable to generating a larger yield of viable protoplasts during the necessary in vitro manipulations of protoplasts if genetic engineering techniques are to be successfully or commercially applied to plant protoplasts in general and to cereal grain plant protoplasts in particular.

There are broadly speaking two main types of threats to protoplast viability using in vitro techniques, chemical damage and physical damage.

Chemical damage to plant protoplasts typically occurs through enzymatic action from crude or only partially purified cell wall degrading enzymes and also from various endogenous enzymes released from targent plant tissues and cells. Currently commercially available cell wall degrading enzymes, such as cellulases and pectinases, necessary to the creation of plant cell protoplasts, since these enzymes are used to remove the plant cell walls from the cells, are not greatly purified and are generally contaminated with proteolytic enzymes. When the currently available cell wall degrading enzymes are used to degrade plant structural tissues, the contaminating proteolytic and lipase enzyme activities often damage or at least degenerate severely the newly exposed protoplast cell membranes. Thus many cells are lysed by the exact mechanism needed to create the protoplasts. Also, even if highly purified cellulases or pectinases were used in cell wall digestion, it is likely that cellular endogenous proteases and other hydrolytic enzymes, such as lipases, would be released into the host medium from the wounded cells or tissues used as starting materials. These endogenous enzymes would act on protoplasts as readily as introduced exogenous enzymes. Furthermore, when protoplasts are exposed to elevated concentrations of osmoticum, which is routinely used in the isolation of protoplast procedure to prevent cell collapse, they often are found to generate high levels of protease and RNase activities. Thus the cycle of protoplast degeneration feeds upon itself as the protoplasts lysed by the contaminated exogenous proteases or by initial wounding induced endogenous proteases or lipases will in turn release large amounts of endogenous cellular proteases and lipases into the surrounding cell tissue medium which then catalyse further damage in the membranes of the newly generated population of protoplasts.

With regard to physical damage, protoplasts are very vulnerable organisms and can be very sensitive and fragile to shearing, shaking or any kind of severe packing or suspension. Cell protoplasts are also very vulnerable to changes in the osmotic pressure of the cell medium which can rapidly cause expansion, and bursting, of the protoplasts, if not carefully monitored.

Both the chemical and physical damage to protoplasts is directly related to the basic biochemical nature of plant protoplast surfaces, i.e. from the fact that the cell membrane instead of the cell wall acts as the cellular envelope in a protoplast. This problem is very analogous to similar problems which exist in the culture of mammalian tissues as single cells and the transfer of mamalian cells into sub-cultures. In the past, it has been believed that particularly specialized media were necessary for the maintenance of plant cell protoplasts and that the media constituents should be primarily derived from plant sources.

An example of use of a plant cell culture media derived from plant sources, in this case microalgae, can be found in European Patent Application No. 0049632. An example of the use of serum in a culture media used for animal cell lines is shown in PCT published application WO 82/02900.

SUMMARY OF THE INVENTION

The present invention is summarized in that a medium for the maintenance and propagation of plant protoplasts in vitro includes therein an effective amount of neutral mammalian blood serum.

The present invention is also summarized in that a method is provided for the in vitro maintenance and propagation of plant protoplasts including the steps of fostering the growth of plant protoplasts in a media supplemented with the biologically active amount of neutral mammalian blood serum.

It is an object of the present invention to provide a medium which fosters the growth of plant cell protoplasts and which yield a far greater yield of viable protoplasts than was possible using other media.

It is another object of the present invention to provide a method for the isolation and propagation of plant cell protoplasts which provides a larger yield and better viable result than previous techniques.

It is yet another object of the present invention to enable the protoplast cultivation of cells from common cereal grain plants such as corn.

It is another object of the present invention to provide such a media and enable such a method using widely and commonly available materials.

Other objects, advantages, and features of the present invention will become apparent from the following specification and accompanying example.

BRIEF DESCRIPTION OF THE DRAWING

The single drawing FIGURE is a graphic representation of the experimental results from a suspension cell line maintenance experiment as described in Example 5 below.

DETAILED DESCRIPTION OF THE INVENTION

In summary, the present invention makes it possible to viably propagate plant protoplasts of many species with good yield by adding to the medium in which the plant protoplasts are cultured a biologically effective amount of whole or fractionated neutral mammalian blood serum. The fact that this medium helps to foster and protect plant protoplast growth is a surprising one. It had previously been believed that plant cell cultures were more properly conducted using media generated from plant derivatives, but it has been found instead that mammalian serum is a very advantageous constituent of the protoplast medium.

It has been found that a media containing between 1 and 25 percent fetal calf serum, and preferably between 5 and 15 percent, is an extremely effective and positive addition to plant cell protoplast maintenance and generation. This additive serves useful purposes in all the steps of plant protoplast separation, isolation and initial propagation and provides a measure of effective control of several of the previously experienced problems in plant protoplast maintenance.

In particular, it has been found that the provision in the plant protoplast medium of a supplement of between 5 and 15 percent neutral fetal calf serum is very generally effective in helping to protect and stabilize plant protoplasts against cellular lysis and deactivation in vitro. It has been found experimentally that the use of a heretofore typical plant protoplast media with mammalian serum added thereto is of benefit in reducing destruction of plant protoplast cells in a variety of stages in the procedure of isolating and propagating protoplasts, including enzymatic digestion of the plant cell wall tissues, the rinsing, isolation and purification of protoplasts from plant cell wall tissue and other cell debris, and in the manipulation, plating and growth of protoplasts and the plant cells in culture. In all stages of these kinds of procedures, widely used in plant cell culture and in genetic manipulation techniques of plants, a far greater yield of viable protoplasts is achievable using a serum supplement to the medium than is achievable without it. Furthermore these advantageous results have been achieved in a variety of useful plant species, including corn, carrot, cotton and tomato.

For use in the present invention it is preferred, but not essential, that the mammalian blood serum be neutral, meaning, in this context, that the serum is partially denatured. To neutralize the serum a two-stage technique is preferably utilized to remove therefrom potentially undesirably biologically active compounds in the untreated serum which could potentially exhibit detrimental effects on plant protoplasts in culture. The first step in the neutralizing process is to use activated charcoal to filter the serum to remove from it the steroids and other biologically active small molecular weight compounds. This step is preferably performed overnight. The second step in the procedure is preferably to use heat treatment (approximately 57° C. for $\frac{1}{2}$ to 4 hours) to deactivate and denature the peptide hormones and growth factors which may be objectionable in the serum. Other serum constituents apparently not detrimental to plant protoplast isolation, maintenance, and growth, such as the serum trypsin-like protease inhibitors, are heat resistant to a limited heat treatment of this type and are not affected by this treatment. Cell biologists working with mammalian cells have also generated several types of neutral blood sera, specifically adapted for use with special mammalian cell culture systems, and most of these sera will be usable in the technique of the present invention on plant protoplasts cultures also. The serum as used in the present invention can be whole or fractionated serum. Whole serum will generally be preferred, for reasons of cost, but appropriate serum fractions still containing protease inhibitors and proper osmotic and viscosity characteristics would also be usable.

While it is not possible to state with certainty the exact chemical and biochemical qualities of the mammalian blood serum which are beneficial to the plant cell protoplasts, there are some general biochemical and physiological characteristics of such a serum which can be fairly characterized as the agents which are most likely to be the most helpful to the maintenance and propagation of plant cell protoplasts. Mammalian blood serum contains high levels of potent trypsin-like protease inhibitors which provide potent anti-proteolytic activity and which act as an agent to inhibit cell lysis in plant as well as animal cells. These inhibitors are of particular value since general protease activity is a strong threat to high protoplast yields, as mentioned above. Mammalian blood serum also includes various large and small molecules, such as albumin, which greatly raise the viscosity of solutions into which they are introduced, and which thus, when introduced into a culture medium, reduce the likelihood of physical damage to cells in the medium which might be caused by shearing, shaking, or packing of the cells. Such an increased viscosity medium thereby reduces the likelihood of cell lysis because of physical damage during experimental manipulations of the protoplast culture. Mammalian blood serum also contains high concentration of soluble salts and other components which are present both intracellularly and intercellularly in mammalian organisms. In vivo in animals there is an exchange of osmotic fluids between the cytosol and the extracellular voids and the maintenance of proper osmotic control is necessary to allow transfers of sugars, amino acids, intermediate metabolites and soluble proteins into and between cells. Since the mammalian serum is the medium which is responsible for the maintenance of proper osmotic and nutritional conditions to allow such transfers, it can also naturally serve as an effective naturally occurring osmoticum and analog for cytosol for cultured mammalian cells in vitro. In accordance with the present invention it has been determined that it can also serve the same purpose for plant cells, once they are removed from their protective plant cell walls.

In general the functioning of the present invention is another indication that the basic cellular physiology observed for plant and animal cells grown in culture may be surprisingly similar once the cells walls are removed from plant cells. While this result is surprising because it was previously believed that vastly different media were necessary for plants as opposed to animal cells, the functioning of the present invention is an indication that the fundamental biochemical differences between plant and animal cells may be somewhat less than previously perceived.

It should be understood within the scope of the present invention in that the particular species of mammalian serum provided is not of critical importance. It has already been generally recognized that mammalian sera from a diverse group of species exhibits similar general biological and biochemical characteristics, independent on whether the source of the serum is of any specific species or any specific maturity level within a species.

One particularly strong advantage of the present invention is that it helps enable protoplast cultivation of cells of cereal grain plants, such as corn. The maintenance of corn propolasts is an important step in the development of techniques to cell culture and to genetically engineer corn and other important cereal grain plants. The isolation and maintenance of corn protoplasts has heretofore been relatively difficult and it has been found that the addition of serum to the protoplast host media significantly lessens that difficulty.

The following examples are illustrative of the scope of the present invention but are not meant or intended to define the same.

EXAMPLE I

Protoplast Isolation

A protoplast isolation technique was practiced on a stable in vitro cell line of carrot cells known as woolc/a. The cells in this cell line are in suspension and are viable as normal plant cells in culture and contain cell walls. To create protoplasts, equal volumes of cell suspensions were digested for 16 hours at room temperature (25° C.) in an enzyme digestion mixture including cellulase, hemicellulase, pectinase and buffering salts. To one sample an amount of neutral, whole fetal calf serum equal to 5% of the sample by volume was added. After the digestion, the yield of newly created protoplasts was collected by differential centrifugation and then counted using a sampling technique on the basis of the number of remaining viable protoplast cells per milliliter of packed volume of starting cell material concentrated. In the sample without the serum, $1.2 \times 10^6$ protoplasts per milliliter were obtained while in the sample with the serum, the corresponding count was $10.1 \times 10^6$ protoplasts per ml, an eightfold better yield.

EXAMPLE 2

Protoplast Isolation

The same protoplast isolation technique was followed as in Example 1 above on a stable BMS-Y2 line of corn cells which were again propagated in a cell suspension and which again normally have cell walls. Again 5% by volume of fetal calf serum was added to the experimental sample and not to the control and both samples were digested, concentrated and counted. The yield for the control was $0.8 \times 10^6$ protoplasts per ml while the yield for the experimental sample was $3.4 \times 10^6$ protoplasts per ml.

EXAMPLE 3

Protoplast Isolation

In this example protoplasts were isolated directly from plant tissue. A sample of leaf mesophyll tissue was removed from the young leaves of a young corn plant. The sample pieces of tissue, about ½ cm² in size, were first conditioned in a nutrient medium, cut into smaller pieces on the order of 0.1 cm² in size, and digested with the enzyme digestion media as also used in Example 1 above in identical experimental and control samples with and without the addition of fetal calf serum. The protoplasts were enriched by differential centrifugation in a rinse medium and again counted. Two separate test procedures were run, and the results were as tabulated below.

| Treatment | Number of Protoplasts per g. of fresh tissue ($\times 10^5$) | |
|---|---|---|
| | Viable | Dead |
| Procedure 1 | | |
| Control | 7.9 | 7.3 |
| Experimental (5% serum) | 35.9 | 6.8 |
| Procedure 2 | | |
| Control | 0.3 | — |
| Experimental 1 (5% serum) | 16.6 | — |
| Experimental 2 (12.5% serum) | 24.5 | — |

EXAMPLE 4

Protoplast Maintenance Regeneration

Previously isolated tomato and corn protoplasts were plated onto a preparation of Gamborg's protoplast medium to which 1 mg/ml of 2,4-D had been added. The controls had no serum added while the experimental plates had neutral, whole, fetal calf serum added to make a total of 5% by volume of the serum. The results were as follows, represented as a percentage of total protoplasts plated.

| Treatment | Cell Wall Formation | Cell Budding or Division | Survival |
|---|---|---|---|
| Tomato: | | | |
| After 5 days: | | | |
| Control | 5% | 2% | 95% |
| Experimental (5% serum) | 30% | 25% | 95% |
| After 10 days: | | | |
| Control | 5% | 2% | 55% |
| Experimental (5% serum) | 45% | 40% | 85% |
| Corn: | | | |
| After 5 days: | | | |
| Control | 30% | 0% | 90% |
| Experimental (5% serum) | 80% | 5% | >90% |

EXAMPLE 5

Cell Suspension Maintenance

Figure 1:
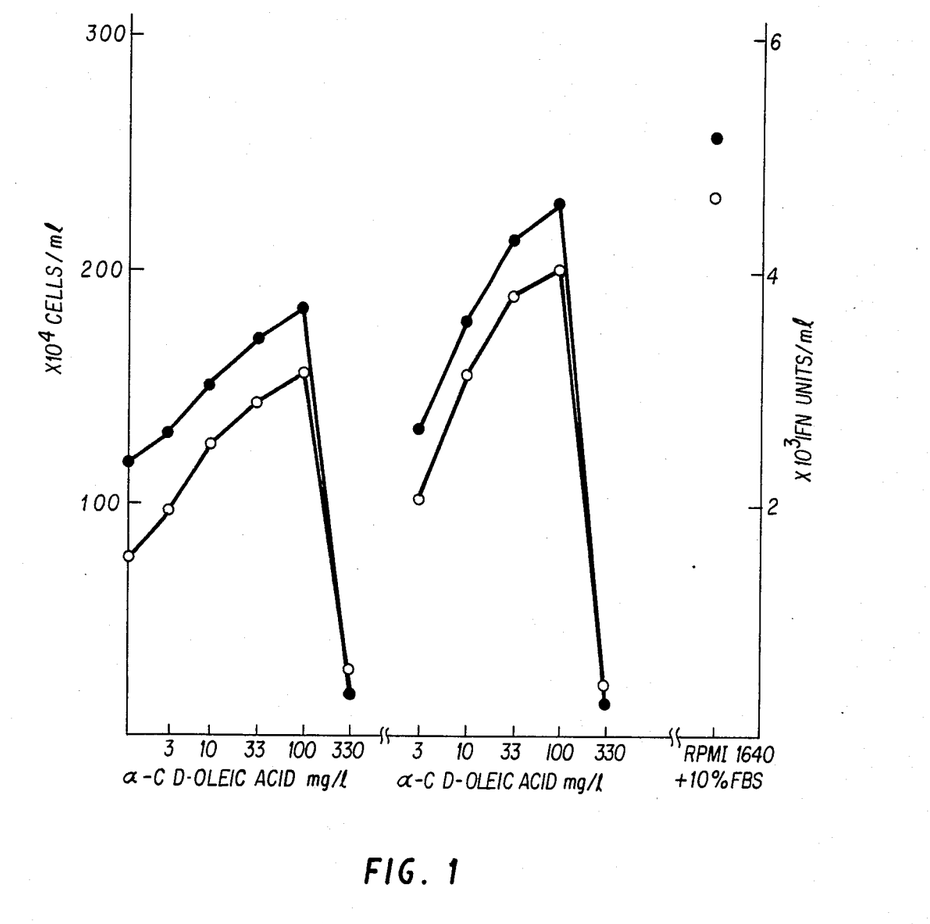
Figure 2:
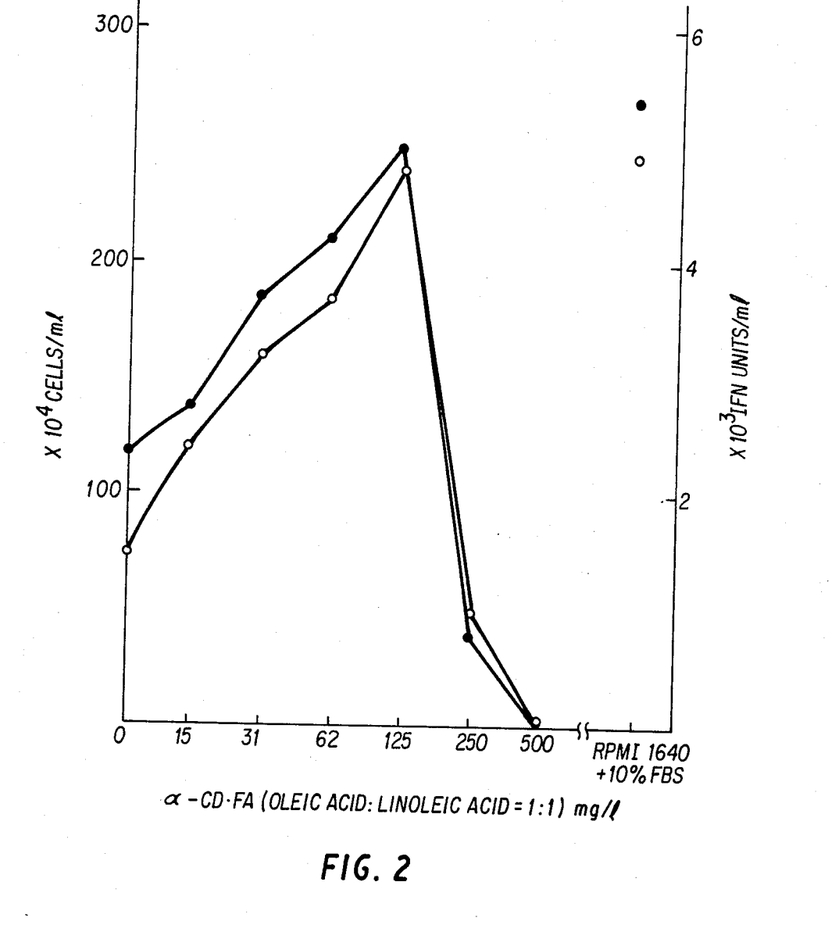
Figure 3:
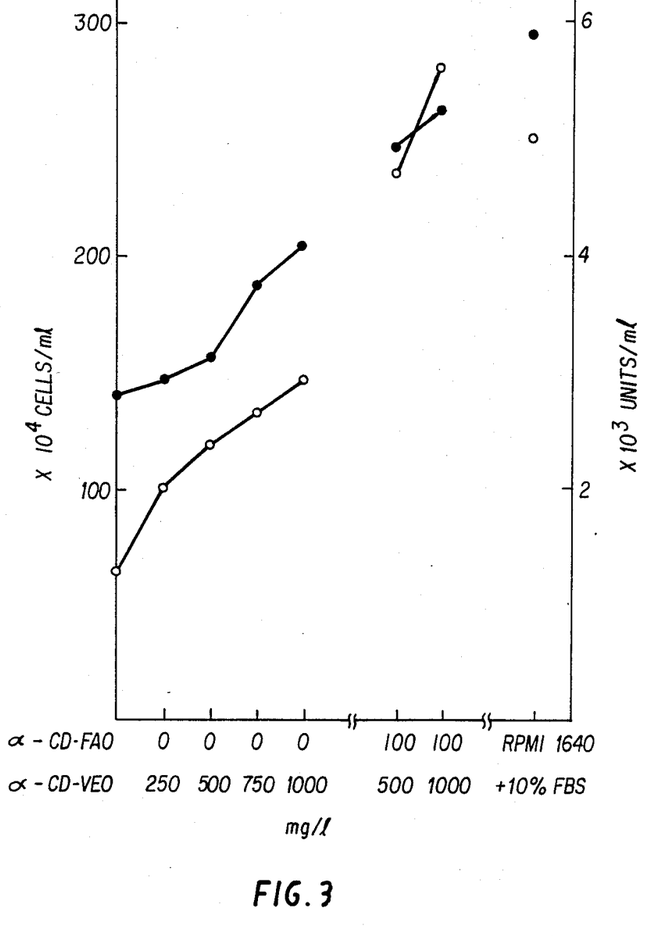
Figure 4:
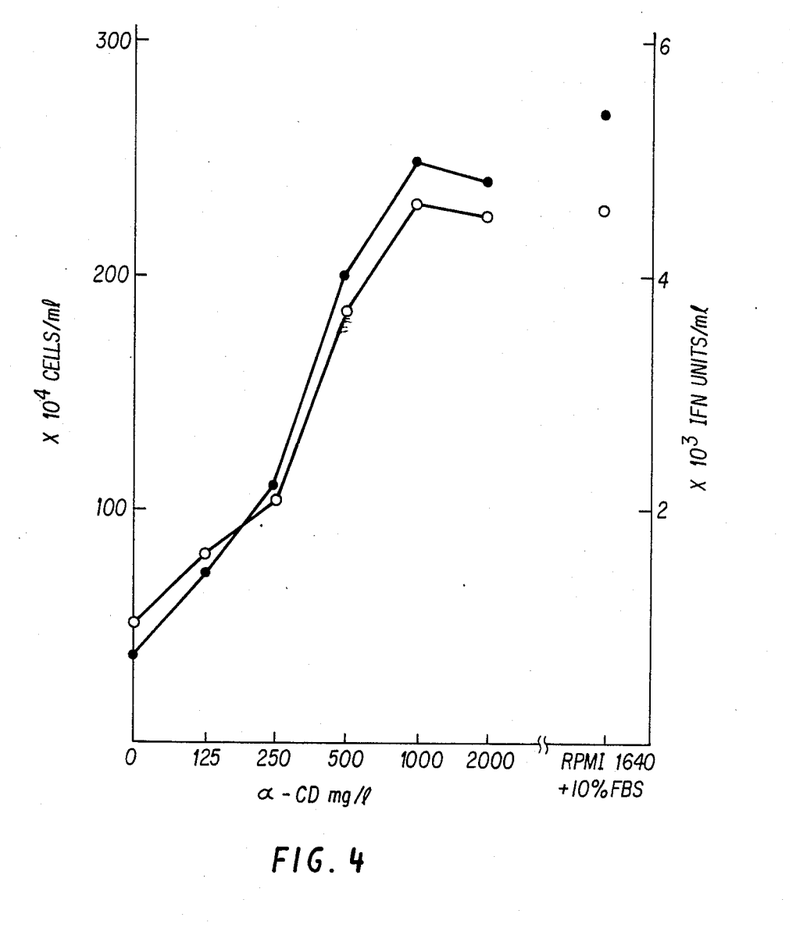
Figure 5:
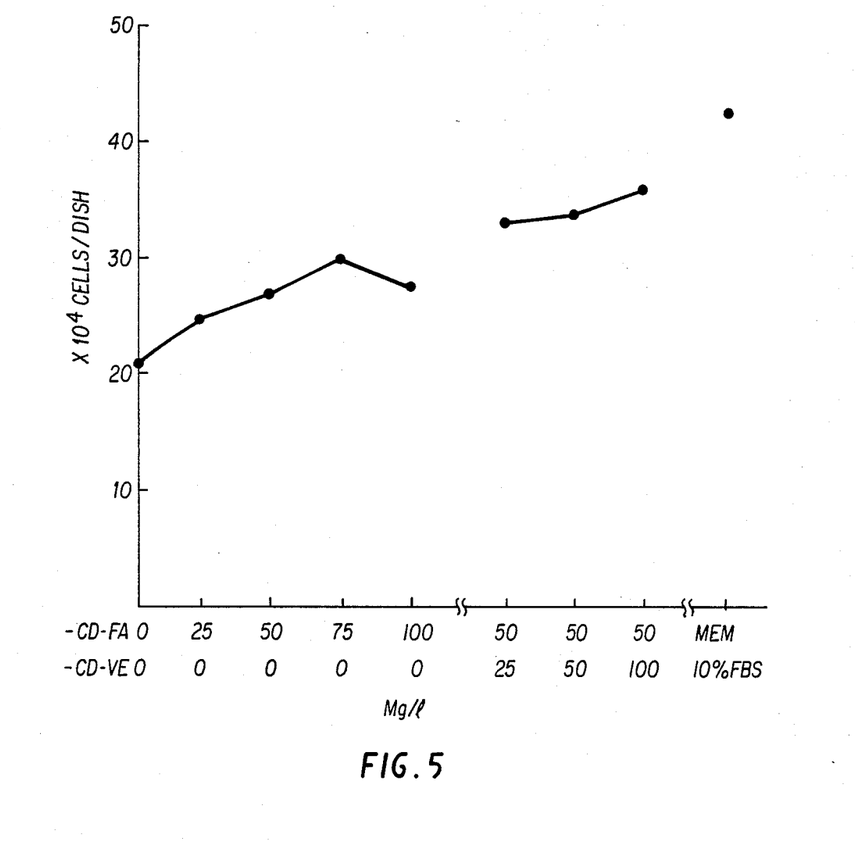

Identical cultures of BMS cell line corn cells were grown in a modified MS medium inoculated with 1 mg/ml of 2,4-D as described in "Plant Regeneration from Tissue Culture of Maize", Green & Phillips, *Crop Science,* Vol. 15, p. 41 (1975). The number of cells was sampled and counted periodically and the results are shown in the graph of the drawing figure. The suspension labeled "Experimental" contained again 5% neutral fetal calf serum by volume, while the control did not.

EXAMPLE 6

Callus Maintenance

Samples of W64A corn cells of mesocotyl tissue from young seedlings were inoculated onto agar plates. The resulting callus cultures were maintained for 45 days, both with and without the addition of 5% fetal calf serum. The serum inoculated samples grew to be approximately 10%–15% greater in size than the controls. After 45 days all cultures were still healthy and viable.

It has also been found that the optimal and the tolerable levels of blood serum used in a culture both vary considerably depending on the species of plant and the stage of cell growth. For example, tentative results seem to indicate that 12.5% by volume of neutral fetal calf serum is very effective in a medium for enzymatic digestion of corn tissue to isolate corn protoplasts, while a 5% level of serum has been found to better foster corn protoplast propogation and growth both in agar plate culture and in suspension. For another example, while the addition of 5% by volume of serum significantly increased cell growth in corn suspension cell lines over a 45 day period, that same level seemed to inhibit growth of carrot cells under similar conditions in a long term culture, although in a short term culture a serum level of 10% by volume seems to improve protoplast yield in carrot during enzymatic protoplast isolation. Thus some empirical experimentation is necessary to establish the precise optimal serum level for a given species, although it is to be understood that the optimal level will be within the range of no less than 1% nor more than 25% serum by volume in the medium.

It is to be understood that the present invention is not limited to the particular embodiments and examples disclosed herein, but embraces all such modified forms thereof as come within the scope of the following claims.

I claim:

1. In a medium for the in vitro isolation and maintenance of plant protoplast cultures including buffer salts, plant nutrients, sugar and plant hormones in aqueous solution wherein the improvement comprises an addition to the medium of a growth promoting amount of mammalian blood serum which has been heat treated to render said serum essentially free of potentially phytotoxic biological substances therefrom.

2. An improvement as claimed in claim 1 wherein the addition of serum is at least 1% of the medium.

3. An improvement as claimed in claim 2 wherein the addition of serum is no more than 25% of the medium.

4. An improvement as claimed in claim 1 wherein the plant is selected from the group consisting of corn, tomato, carrot and cotton.

5. In a method wherein protoplasts are cultivated in a media and are isolated wherein the improvement comprises adding to the protoplast medium a growth promoting amount of mammalian blood serum which has been heat treated to render said serum essentially free of potentially phytotoxic biological sustances therefrom.

6. A method as claimed in claim 5 wherein the adding step includes adding no less than 1% and no more than 25% serum to the medium.

7. A method as claimed in claim 5 further comprising the step of neutralizing the serum by filtering with activated charcoal and by heat treatment at approximately 57° C.

8. A method as claimed in claim 5 wherein the plant is a cereal plant.

9. A method as claimed in claim 5 wherein the plant is selected from the group consisting of corn, tomato, cotton, and carrot.

10. A method as claimed in claim 5 wherein the serum is neutral whole serum.

* * * * *